(12) United States Patent
Okamoto et al.

(10) Patent No.: US 8,586,323 B2
(45) Date of Patent: Nov. 19, 2013

(54) BLOOD COAGULATION PROMOTER AND BLOOD COLLECTION TUBE COMPRISING A POLYOXYALKYLENE GLYCERIN DERIVATIVE

(75) Inventors: Ryusuke Okamoto, Shunan (JP); Katsuya Togawa, Shunan (JP); Hironobu Isogawa, Tokyo (JP)

(73) Assignee: Sekisui Chemical Co., Ltd., Osaka (JP)

( * ) Notice: Subject to any disclaimer, the term of this patent is extended or adjusted under 35 U.S.C. 154(b) by 1255 days.

(21) Appl. No.: 10/548,541

(22) PCT Filed: Apr. 21, 2004

(86) PCT No.: PCT/JP2004/005689
§ 371 (c)(1), (2), (4) Date: Sep. 12, 2005

(87) PCT Pub. No.: WO2004/097407
PCT Pub. Date: Nov. 11, 2004

(65) Prior Publication Data
US 2006/0171915 A1 Aug. 3, 2006

(30) Foreign Application Priority Data
Apr. 25, 2003 (JP) .................................. 2003-122756

(51) Int. Cl.
*C12Q 1/56* (2006.01)
*G01N 33/86* (2006.01)

(52) U.S. Cl.
USPC .............................................. 435/13; 436/69

(58) Field of Classification Search
None
See application file for complete search history.

(56) References Cited

U.S. PATENT DOCUMENTS

| 4,145,318 A | 3/1979 | Ohashi et al. |
| 4,163,086 A | 7/1979 | Narayan et al. |
| 4,440,705 A | 4/1984 | Nissen et al. |
| 4,856,533 A | 8/1989 | Anraku et al. |
| 4,861,712 A | 8/1989 | Bartl et al. |
| 5,888,824 A | 3/1999 | Isogawa et al. |

FOREIGN PATENT DOCUMENTS

| EP | 1 215 494 A2 | 6/2002 |
| EP | 1 215 494 A3 | 9/2002 |
| JP | 05-10095 | * 2/1993 |
| JP | 5-103772 | 4/1993 |
| JP | 2000-292421 A | 10/2000 |
| JP | 2001-269328 A | 10/2001 |
| JP | 2002-82112 A | 3/2002 |

OTHER PUBLICATIONS

CHemical Abstracts Registry of ADEKA CARPOL G 4000, accessed Sep. 19, 2008.*
International Search Report.
Supplementary European Search Report for the Application No. EP 04 72 8643 dated Apr. 3, 2009.
Official Communication for the Application No. EP 04 728 643.0 from European Patent Office dated Aug. 21, 2009.

* cited by examiner

*Primary Examiner* — Sandra Saucier
(74) *Attorney, Agent, or Firm* — Cheng Law Group, PLLC

(57) ABSTRACT

The present invention provides a blood coagulation promoter capable of exerting both excellent blood coagulation promoting ability and excellent blood clot detaching ability; and a blood collection tube accommodating the blood coagulation promoter.

The present invention provides a blood coagulation promoter which includes a hardly water soluble polyoxyalkylene derivative; a partially saponificated polyvinyl alcohol; at least one substance selected from the group consisting of adsorptive inorganic substances and hydrolases capable of hydrolyzing a bond between Arg and an arbitrary amino acid reside and/or a bond between Lys and an arbitrary amino acid residue in a peptide chain; a polyvinylpyrrolidone; and preferably a water-soluble silicone oil, and a blood collection tube in which the blood coagulation promoter is accommodated in a tubular vessel having a bottom.

11 Claims, 1 Drawing Sheet

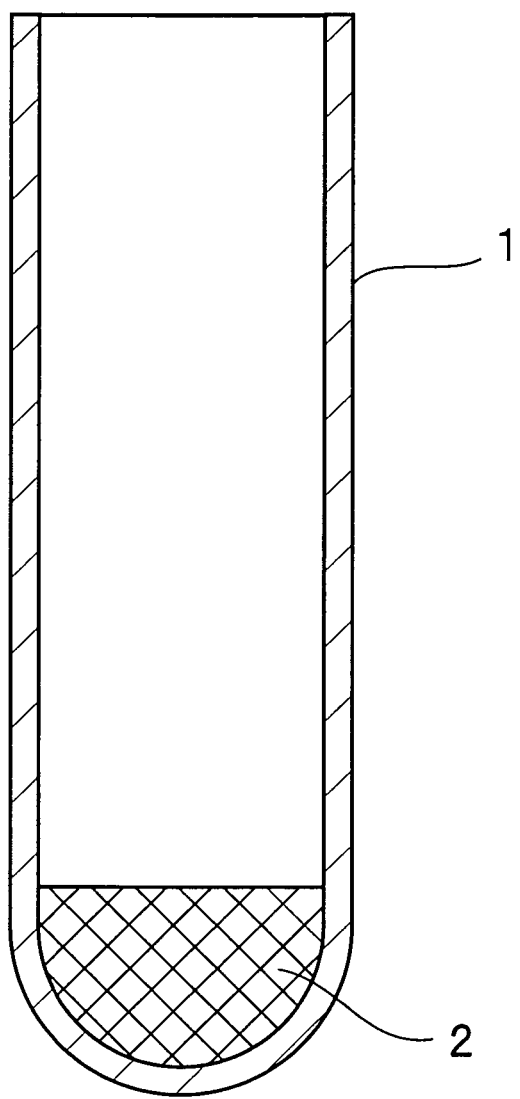

BLOOD COAGULATION PROMOTER AND BLOOD COLLECTION TUBE COMPRISING A POLYOXYALKYLENE GLYCERIN DERIVATIVE

FIELD OF THE INVENTION

The present invention relates to blood coagulation promoters and blood collection tubes, and more particularly to a blood coagulation promoter having excellent blood coagulation promoting ability and blood clot detaching ability, and a blood collection tube accommodating the blood coagulation promoter.

BACKGROUND ART

In usual serum examinations, blood collected into a blood collection tube is caused to coagulate, and then centrifuged for separating an intended blood component.

Such a blood collection tube desirably has blood coagulation promoting ability that allows the collected blood to coagulate in short time, and blood clot detaching ability that prevents the coagulated blood from adhering to the inner wall of the blood collection tube in the form of blood clots while detaching adhered blood clots. As such a blood collection tube, blood collection tubes whose inner wall is processed in various manners have been reported.

For example, Japanese Examined Patent Publication HEI-5-10095 discloses a blood collection tube in which an inner wall of a vessel made of a specific material is coated with a blood coagulation promoter comprising a water-insoluble silicone oil, polyvinylpyrrolidone and an adsorptive inorganic substance.

Japanese Unexamined Patent Publication HEI 5-103772 discloses a blood collection tube in which an inner wall of a vessel made of a specific material is coated with a blood coagulation promoter via a water-soluble silicone oil.

These reported that coating the inner wall of a blood collection tube with the coagulation promoter as described above enables the collected blood to coagulate in short time and prevents blood clots from adhering to the inner wall of the tube.

However, in such a blood collection tubes, it was necessary to apply the silicone oil in high concentration so as to prevent blood clots from adhering to the inner wall of the tube. To be more specific, concentration of the silicone oil to be applied to the inner wall of the blood collection tube was as high as $5.0 \times 10^{-6}$ to $1.0 \times 10^{-5}$ g/cm$^2$. This led the problem that the presence of silicone oil at high concentration may adversely affect test values.

Another problem was that when these blood collection tubes have a plug member, blood clots come into adhered to the plug member upon coagulation of the blood collected into the blood collection tube.

DISCLOSURE OF THE INVENTION

In consideration of the above problems accompanying the conventional art, it is an object of the present invention to provide a blood coagulation promoter capable of exerting both excellent blood coagulation promoting ability and excellent blood clots detaching ability, and a blood collection tube accommodating the blood coagulation promoter.

The blood coagulation promoter according to the present invention includes a hardly water soluble polyoxyalkylene derivative; at least one substance selected from the group consisting of (a) adsorptive inorganic substances and (b) hydrolases capable of hydrolyzing a bond between Arg and an arbitrary amino acid reside and/or a bond between Lys and an arbitrary amino acid residue in a peptide chain; and polyvinylpyrrolidone.

In a specific aspect of the blood coagulation promoter according to the present invention, $3 \times 10^{-3}$ to 7 parts by weight of a water-soluble silicone oil is further included, relative to 100 parts by weight of the sum of the hardly water soluble polyoxyalkylene derivative; at least one substance selected from the group consisting of (a) adsorptive inorganic substances and (b) hydrolases capable of hydrolyzing a bond between Arg and an arbitrary amino acid reside and/or a bond between Lys and an arbitrary amino acid residue in a peptide chain; and the polyvinylpyrrolidone.

Preferably, the blood coagulation promoter according to the present invention further includes a partially saponificated polyvinyl alcohol.

In a specific aspect of the blood coagulation promoter according to the present invention, $3 \times 10^{-3}$ to 7 parts by weight of a water-soluble silicone oil is further included, relative to 100 parts by weight of the sum of the hardly water soluble polyoxyalkylene derivative; the partially saponificated polyvinyl alcohol; at least one substance selected from the group consisting of (a) adsorptive inorganic substances and (b) hydrolases capable of hydrolyzing a bond between Arg and an arbitrary amino acid reside and/or a bond between Lys and an arbitrary amino acid residue in a peptide chain; and the polyvinylpyrrolidone.

The blood collection tube according to the present invention is characterized in that the blood coagulation promoter constituted according to the present invention is accommodated in a vessel.

The present invention will now be explained in detail.

A blood coagulation promoter according to the present invention consists essentially of a hardly water soluble polyoxyalkylene derivative; at least one substance selected from the group consisting of (a) adsorptive inorganic substances and (b) hydrolases capable of hydrolyzing a bond between Arg and an arbitrary amino acid reside and/or a bond between Lys and an arbitrary amino acid residue in a peptide chain; and polyvinylpyrrolidone.

The hardly water soluble polyoxyalkylene derivative used in the blood coagulation promoter of the invention serves as a blood clot adhesion preventing component.

Examples of the hardly water soluble polyoxyalkylene derivative include various compounds derived from known polyoxyalkylenes, such as butanol derivative of polyoxyalkylene and glycerin derivative of polyoxyalkylene.

The hardly water soluble polyoxyalkylene derivative is preferably hardly soluble in water and blood, and more preferably insoluble in water and blood.

Since the hardly water soluble polyoxyalkylene derivative serves as a blood clot adhesion preventing component, it is possible to prevent blood clots from adhering to the inner wall of the vessel after coagulation and to desirably separate between blood clots and serum without restricting movement of the blood clots during centrifugal separation.

The blood coagulation promoter of the present invention preferably includes a partially saponificated polyvinyl alcohol. The partially saponificated polyvinyl alcohol is used as a blood clot detaching component.

As the partially saponificated polyvinyl alcohol, known compounds can be used, for example, a compound obtained by saponificating polyvinyl acetate with sodium hydroxide.

Saponification degree of the partially saponificated polyvinyl alcohol is preferably from 75 to 98% by mole, and more preferably from 85 to 95% by mole.

If the saponification degree of the partially saponificated polyvinyl alcohol is less than 75% by mole, the partially saponificated polyvinyl alcohol may adversely affect test values because solubility in blood and surface acting effect increase.

On the other hand, if the saponification degree of the partially saponificated polyvinyl alcohol is more than 98% by mole, blood clot detaching ability may become difficult to be sufficiently exerted.

The degree of polymerization of the partially saponificated polyvinyl alcohol is preferably in the range of 300 to 3,500, and more preferably in the range of 500 to 2,500.

If the degree of polymerization of the partially saponificated polyvinyl alcohol is less than 300, solubility is too high which may impair the blood clot detaching ability. If the degree of polymerization is more than 3,500, the viscosity is too high to achieve uniform application to the inner wall of the vessel difficult.

The adsorptive inorganic substance (a) used in the blood coagulation promoter of the present invention is uses as a blood coagulation component.

The adsorptive inorganic substance is preferably insoluble in water. Water insolubility of the adsorptive inorganic substance can minimize the influence on test results.

The adsorptive inorganic substance is preferably in powder form. By using that the adsorptive inorganic substance is in powder form, a specific surface area of the adsorptive inorganic substance increases, resulting that the blood coagulation promoter of the present invention can coagulate the blood in shorter time.

The specific surface area of the adsorptive inorganic substance is preferably in the range of 10 to 1000 $m^2/g$, and more preferably in the range of 50 to 500 $m^2/g$.

An average particle size of the adsorptive inorganic substance is preferably less than or equal to 50 μm, and more preferably less than or equal to 10 μm. If the average particle size of the adsorptive inorganic substance is more than 50 μm, coagulation of blood in short time may become difficult to achieve.

Examples of such adsorptive inorganic substance include silica, glass, kaolin, celite and bentonite.

These adsorptive inorganic substances may be used singly or in combination of two or more kinds.

Among these adsorptive inorganic substances, silica is preferably used. Silica is preferably in powder form, and more preferably in porous form containing 20% by weight or more of amorphous components.

Such silica is preferably hydrophobic. Use of the hydrophobic silica makes it possible to prevent hemolysis due to decreased solubility in blood, and allows blood to coagulate in short time due to improved dispersibility in blood.

Preferably, the adsorptive inorganic substance has high dispersibility in blood. High dispersibility in blood allows blood to coagulate in shorter time.

If the amount of the above adsorptive inorganic substance is too small, the time required for blood coagulation may increase, or coagulation may become insufficient, whereas if the amount is too large, test values may be adversely affected. Therefore, the amount is preferably in the range of $1 \times 10^{-6}$ to $1 \times 10^{-3}$ g and more preferably in the range of $1 \times 10^{-5}$ to $1 \times 10^{-4}$, per 1 mL of blood.

The (b) hydrolases are proteases, and those capable of hydrolyzing a bond between Arg and an arbitrary amino acid residue and/or a bond between Lys and an arbitrary amino acid residue in a peptide chain are used.

Examples of the hydrolases include serine proteases such as trypsin, thrombin, rattle snake thrombin-like serine protease; thiol proteases such as cathepsin B and ficin; metal proteases such as kininase I, with serine proteases in particular being preferably used. If the amount of the hydrolase is small, the time required for blood coagulation may increase or coagulation may be insufficient. Contrarily, if the amount is large, test values may be adversely affected. Therefore, the use amount of the hydrolase is preferably in the range of 0.1 to 100 U (unit), and more preferably 0.5 to 50 U (unit) per 1 mL of blood.

The blood coagulation promoter of the present invention may further include an amino acid. The amino acid in the present invention is used as a stabilizer for the above hydrolase, and for example, glycine, β-alanine, L-serine, L-tryptophan and the like are preferably used. If the amount of the amino acid is small, the effect of keeping the stability of the hydrolase may be insufficient, whereas if the amount is large, test values may be adversely affected. Therefore, the amount of the amino acid is preferably in the range of 0.01 to 10 mg, and more preferably in the range of 0.05 to 5 mg per 1 U of the hydrolase.

The blood coagulation promoter of the present invention may further include an amine salt and/or an organic compound having a quaternary nitrogen. The amine salt and/or organic compound having a quaternary nitrogen functions as a heparin neutralizer that adheres, neutralizes and inactivates heparin.

An amine constituting the amine salt may be any of primary amines, secondary amines and tertiary amines, and an acid constituting the amine salt may be inorganic acids and organic acids. Examples of the inorganic acids include halogenated hydrogen acids such as hydrochloric acid, sulfuric acid and sulfurous acid, and examples of the organic acids include formic acid and acetic acid. An organic group of the amine salt is usually an alkyl group, however, it may be a hydrocarbon group containing a hetero element such as imino group and ether group. The amine salt may be an intramolecular salt. Concrete examples of a preferable amine salt include hexadecyldimethylamine hydrochloride and tetradecyl(aminoethyl)glycine.

As the organic compound having a quaternary nitrogen, tetraalkylammonium can be exemplified, however, compounds having an aryl group instead of an alkyl group, or compounds having a hydrocarbon group containing a hetero element such as imino group or ether group can also be recited. Preferred examples of the organic compound having a quaternary nitrogen include dodecyltrimethyl ammonium chloride, however, organic polymers such as polycation having a quaternary nitrogen can also be used. If the amount of the organic compound is too small, blood containing heparin may fail to coagulate because heparin is not neutralized, whereas if the amount is too large, test values may be adversely affected. Therefore, the amount is preferably in the range of 0.005 to 10 mg and more preferably in the range of 0.01 to 5 mg per 1 mL of blood.

The blood coagulation promoter of the present invention may further include an antifibrirolytic agent and/or antiplasmin agent. Accordingly, fibrin degrading effect of the plasmin which is antagonistically generated in the process of blood coagulation reaction will be inhibited. This in turn promotes coagulation of the blood, and keeps the coagulation condition stable during coagulation.

As the antifibrirolytic agent and/or antiplasmin agent, for example, aprotinin, soybean trypsin inhibitor, e-aminocapronic acid, p-aminomethyl benzoic acid, aminomethyl cyclohexane carbonic acid and the like can be used singly or in combination. These are included in the blood coagulation promoter in such an amount that will not influence on a clinical test using the obtainable serum. For example, it is preferable that aprotinin is included in a ratio of about 100 to 600 KIU (unit) per 1 mL of blood; soybean trypsin inhibitor included in a ratio of about 500 to 4,000 FU (unit) per 1 mL of blood; e-aminocapronic acid, p-aminomethyl benzoic acid and aminomethyl cyclohexane carbonic acid each included in a ratio of about $1 \times 1.0^{-8}$ to $1 \times 10^{-2}$ g per 1 mL of blood.

Polyvinylpyrrolidone used in the blood coagulation promoter of the present invention is used as a dispersing agent for dispersing the above (a) adsorptive inorganic substances or (b) hydrolases.

As such polyvinylpyrrolidone, N-vinylpyrrolidone and the like can be exemplified.

The weight-average molecular weight of the polyvinylpyrrolidone is preferably in the range of 10,000 to 600,000, and more preferably in the range of 30,000 to 500,000.

If the weight-average molecular weight of the polyvinylpyrrolidone is less than 10,000, hemolysis may occur. If the weight-average molecular weight is more than 600,000, dispersibility of the adsorptive inorganic substance or the like in blood is decreased, which may make the blood difficult to coagulate in short time.

Preferably, the polyvinylpyrrolidone has high solubility in the compounds constituting the blood coagulation promoter of the present invention, in particular in the water-soluble silicone oil.

Such high solubility in the compounds constituting the blood coagulation promoter enables the blood coagulation promoter of the present invention to exist in stable condition even when mixed with a solvent such as water, while preventing these compounds from adhering to the surface of the adsorptive inorganic substance to hinder coagulation of the blood.

Blending amount of each compound constituting the blood coagulation promoter of the present invention, relative to 100 parts by weight of the hardly water soluble polyoxyalkylene derivative are preferably as follows: 1 to $2 \times 10^4$ parts by weight of partially saponificated polyvinyl alcohol; $4 \times 10^2$ to $5 \times 10^4$ parts by weight of at least one substance selected from the group consisting of adsorptive inorganic substances and hydrolases capable of hydrolyzing a bond between Arg and an arbitrary amino acid reside and/or a bond between Lys and an arbitrary amino acid residue in a peptide chain; and $2 \times 10^2$ to $4 \times 10^4$ parts by weight of polyvinylpyrrolidone. When the partially saponificated polyvinyl alcohol is not blended, the compounds other than the partially saponificated polyvinyl alcohol are preferably blended in the amounts as described above.

In the above blending amounts, it is more preferred that the blending amount of the partially saponificated polyvinyl alcohol, relative to 100 parts by weight of the hardly water soluble polyoxyalkylene derivative is in the range of 10 to $2 \times 10^3$ parts by weight.

More preferably, the blending amount of at least one substance selected from the group consisting of adsorptive inorganic substances and hydrolases capable of hydrolyzing a bond between Arg and an arbitrary amino acid reside and/or a bond between Lys and an arbitrary amino acid residue in a peptide chain, relative to 100 parts by weight of the hardly water soluble polyoxyalkylene derivative is preferably in the range of $7 \times 10^2$ to $5 \times 10^3$ parts by weight, and the blending amount of the polyvinylpyrrolidone is more preferably in the range of $5 \times 10^2$ to $4 \times 10^3$ parts by weight.

The blood coagulation promoter of the present invention may be added with a small amount of water-soluble silicone oil as a blood clot adhesion preventing component.

By using the water-soluble silicone oil, more excellent clot detaching ability is exerted against the inner wall of the tube in a blood collection tube having a plug member, as well as against the plug member.

As the water-soluble silicone oil, any silicone oil can be used without limitation insofar as it is highly hydrophilic, and silicon oils modified to be hydrophilic by introduction of a polar group can be exemplified.

Examples of such polar group include hydroxyl group, amino group, carboxyl group, epoxy group and ether group.

Examples of silicone oil before modification include aliphatic silicone oils such as dimethylpolysiloxane and methylhydrodienepolysiloxane, and aromatic silicone oils such as methylphenolpolysiloxane.

Among these water-soluble silicone oils, dimethylpolysiloxane modified with ether group is preferably used.

These water-soluble silicone oils may be used singly or in combination of two or more kinds.

When the blood coagulation promoter of the present invention includes a water-soluble silicone oil, the blending amount of the water-soluble silicone oil is preferably in the range of $3 \times 10^{-3}$ to 7 parts by weight and more preferably in the range of $3 \times 10^{-2}$ to 5 parts by weight, relative to 100 parts by weight of the sum of the hardly water soluble polyoxyalkylene derivative; at least one substance selected from the group consisting of (a) adsorptive inorganic substances and (b) hydrolases; and the polyvinylpyrrolidone.

When the aforementioned partially saponificated polyvinyl alcohol is blended, the water-soluble silicone oil is preferably in the range of $3 \times 10^{-3}$ to 7 parts by weight and more preferably in the range of $3 \times 10^{-2}$ to 5 parts by weight, relative to 100 parts by weight of the sum of the hardly water soluble polyoxyalkylene derivative; the partially saponificated polyvinyl alcohol; at least one substance selected from the group consisting of (a) adsorptive inorganic substances and (b) hydrolases; and the polyvinylpyrrolidone.

If the blending amount of the water-soluble silicone oil is more than 7 parts by weight, test values may be affected. If the blending amount is less than $3 \times 10^{-3}$ parts by weight, it may become difficult to exert sufficient blood clot detaching ability against the plug member of the blood collection tube.

The blood collection tube of the present invention may accommodate a serum separating agent as necessary.

Coagulation of blood is promoted when the blood is brought into contact with the blood coagulation promoter of the present invention.

Examples of the method for bringing blood into contact with the blood coagulation promoter include, but not limited to, (1) a method of adding the collected blood to a tubular vessel having a bottom such as a blood collection tube preliminarily accommodating the blood coagulation promoter of the present invention; and (2) a method of adding the blood coagulation promoter of the present invention into a tubular vessel having a bottom such as a blood collection tube accommodating the collected blood.

In these methods, the method of (1) is preferably used. The blood collection tube preliminarily accommodating the blood coagulation promoter is one aspect of the present invention. FIG. 1 is a front section view showing one example of a blood collection tube according to the preset invention. A blood coagulation promoter 2 according to the present invention is accommodated in a tubular blood collection tube 1 having a bottom. The blood collection tube 1 may be a vacuum blood collection tube accommodating the blood coagulation promoter 2.

It may be a blood collection tube having a plug member. When the blood collection tube has a plug member, it is preferred that the blood coagulation promoter is also applied to the plug member.

Examples of the material for the blood collection tube include, but not limited to, resins such as polyethylene terephthalate, metals and glass.

As the method for accommodating the blood coagulation promoter in the blood collection tube, any method can be used without limitation, and exemplification can be made with a method wherein a solution obtained by dispersing the blood coagulation promoter of the present invention in a solvent such as water is applied to the inner wall of the blood collection tube and then solvent is removed by drying.

As the method for applying the blood coagulation promoter to the inner wall of the blood collection tube, a spray method, a dipping method and the like can be exemplified.

The amount of the hardly water soluble polyoxyalkylene derivative in the blood coagulation promoter after the blood coagulation promoter of the invention has been applied to the inner wall of the blood collection tube is preferably in the range of $1 \times 10^{-9}$ to $1 \times 10^{-5}$ g/cm$^2$ and more preferably in the range of $1 \times 10^{-8}$ to $1 \times 10^{-6}$ g/cm$^2$, on the basis of the area on the inner wall. If the amount of the hardly water soluble polyoxyalkylene derivative is less than $1 \times 10^{-9}$ g/cm$^2$, it may become difficult to exert sufficient blood clot detaching ability against the inner wall of the tube. If the amount of the hardly water soluble polyoxyalkylene derivative is more than $1 \times 10^{-5}$ g/cm$^2$, test values may be adversely affected.

The amount of the partially saponificated polyvinyl alcohol in the blood coagulation promoter after the blood coagulation promoter of the invention has been applied to the inner wall of the blood collection tube is preferably in the range of $1 \times 10^{-9}$ to $1 \times 10^{-5}$ g/cm$^2$ and more preferably in the range of $1 \times 10^{-8}$ to $1 \times 10^{-6}$ g/cm$^2$, on the basis of the area on the inner wall. If the amount of the partially saponificated polyvinyl alcohol is less than $1 \times 10^{-9}$ g/cm$^2$, it may become difficult to exert sufficient blood clot detaching ability against the inner wall of the tube. If the amount of the partially saponificated polyvinyl alcohol is more than $1 \times 10^{-5}$ g/cm$^2$, dispersibility of the adsorptive inorganic substance decreases, making blood difficult to coagulate in short time in some cases.

The amount of the polyvinylpyrrolidone in the blood coagulation promoter after the blood coagulation promoter of the invention has been applied to the inner wall of the blood collection tube is preferably in the range of $1 \times 10^{-7}$ to $1 \times 10^{-4}$ g/cm$^2$ and more preferably in the range of $1 \times 10^{-6}$ to $1 \times 10^{-5}$ g/cm$^2$, on the basis of the area on the inner wall. If the amount of the polyvinylpyrrolidone is less than $1 \times 10^{-7}$ g/cm$^2$, the surface of the adsorptive inorganic substance is covered with the blood clot adhesion preventing component and direct contact with the blood becomes difficult to occur. This may make it difficult for blood to coagulate in short time. If the amount of the polyvinylpyrrolidone is more than $1 \times 10^{-4}$ g/cm$^2$, dispersibility of the adsorptive inorganic substance decreases, making blood difficult to coagulate in short time in some cases.

The amount of the water-soluble silicone oil in the blood coagulation promoter after the blood coagulation promoter of the invention has been applied to the inner wall of the blood collection tube is preferably in the range of $1 \times 10^{-10}$ to $1 \times 10^{-6}$ g/cm$^2$ and more preferably in the range of $1 \times 10^{-9}$ to $5 \times 10^{-7}$ g/cm$^2$, on the basis of the area on the inner wall. If the amount of the water-soluble silicone oil is less than $1 \times 10^{-10}$ g/cm$^2$, when the blood collection tube has a plug member such as rubber plug, it may become difficult to exert sufficient blood clot detaching ability against the plug member. Furthermore, when the amount of the silicone oil is more than $1 \times 10^{-6}$ g/cm$^2$, test values may be adversely affected.

As the method for coagulating the blood using the blood collection tube of the present invention, a method wherein after collecting blood in the blood collection tube of the present invention and sealing the same, the blood collection tube is left at room temperature to allow the blood coagulate, and a method wherein after collecting blood, the blood is allowed to coagulate by addition of an additive such as serum separating agent can be exemplified.

Preferably, the blood collection tube of the present invention is capable of conducting centrifugal separation following coagulation of the blood. This makes it possible to readily separate the coagulated blood.

BRIEF DESCRIPTION OF THE DRAWINGS

FIG. 1 is a front section view showing one example of a blood collection tube according to the present invention.

BEST MODE FOR CARRYING OUT OF THE INVENTION

The present invention will be explained more specifically by way of examples, however, the present invention is not limited to these examples.

In the following Examples and Comparative examples, the following compounds were used as blending components for the blood coagulation promoter.

Hardly Water Soluble Polyoxyalkylene Derivative
Glycerin derivative of polypropylene glycol
("ADEKA CARPOL G4000", product of ASAHI DENKA CO., LTD.)
Partially Saponificated Polyvinyl Alcohol
(saponification degree: 87 to 89% by mole, polymerization degree: 1,000)
Polyvinylpyrrolidone
(weight-average molecular weight: 45,000)
Adsorptive Inorganic Substance
micro powder silica
Hydrolase
thrombin
(THROMBIN MOCHIDA, product of MOCHIDA PHARMACEUTICAL CO., LTD.)
Water-Soluble Silicone Oil
dimethylpolysiloxane modified with ether group
("SF 8410 oil", product of Dow Corning Toray Silicone Co., Ltd)
Solvent
ion exchange water Examples 1 to 12, Comparative Examples 1 to 3

(Preparation of Blood Coagulation Promoter)

Blood coagulation promoters were prepared by mixing each compound in ion exchange water which is a solvent so as to give the compositions as shown in Table 1 and Table 2.

(Manufacture of Blood Collection Tube)

Each 20 mL of blood coagulation promoter prepared in the respective Examples and Comparative examples was uniformly applied to the inner wall of a 10-mL blood collection tube intended for separation of serum, made of polyethylene terephthalate by a spray method, followed by air drying, to prepare a blood collection tube.

The following evaluations were conducted using each blood collection tube as a test blood collection tube.

(Measurement of Blood Coagulation Time)

For the test blood collection tubes prepared in Examples 1 to 12 and Comparative examples 1 to 3, 3 mL of human fresh blood was collected in each test blood collection tube, thereafter the tube was sealed with Parafilm (Registered Trademark), and the sample was mixed by inverting five times and left at 25° C. The time (unit: minute) required for achieving complete coagulation of blood from the end of blood collection was measured. Complete coagulation was determined when the upper surface of the blood no longer moves even if the test blood collection tube is inclined, and the blood no longer flows out even if the tube is kept bottom up. Also evaluation was made for the case where the above operation was performed except that mixing by inversion was conducted only once. For the test blood collection tubes prepared in Examples 13 to 24, first the test blood collection tube was evacuated and the inner pressure was adjusted so as to give 3 mL of blood collection amount, and then the tube was hermetically sealed with a butyl rubber plug. In this test blood collection tube, 3 mL of human fresh blood was collected, and then mixed by inverting five times, and left at 25° C. Then the time (unit: minute) required for achieving complete coagulation of blood from the end of blood collection was measured. Complete coagulation was determined when the upper surface of the blood no longer moves even if the test blood collection tube is inclined, and the blood no longer flows out even if the tube is kept bottom up. Also evaluation was made for the case where the above operation was performed except that mixing by inversion was conducted only once.

(Observation of Hemolysis and Blood Clots)

Each test blood collection tube having subjected to blood coagulation measurement was placed in a centrifugal separator, and centrifuged at 3000 rpm for 5 minutes. Whether or not hemolysis occurred in the serum after centrifugation was visually checked. Whether blood clots adhered or not on the inner wall of the test blood collection tube after centrifugation and on the rubber plug was visually checked.

When adhesion of blood clots or hemolysis was observed, it was evaluated as "YES", and when not observed, it was evaluated as "NO".

(Measurement of Ferritin)

For the test blood collection tube having subjected to mixing by inverting five times in the measurement of blood coagulation time, 3 mL of serum containing known concentration of ferritin (56 ng/mL) was added to the test blood collection tube after centrifugation, and mixed well. Then a ferritin measuring reagent ("FER-Latex X2" manufactured by DENKA SEIKEN Co., Ltd.) was added, and concentration of ferritin (unit: ng/mL) was determined by an automatic analyzer ("7170S" manufactured by HITACHI, LTD.).

The results of measurement are shown in Table 1, Table 2 and Table 3.

TABLE 1

| | | Unit | Example 1 | 2 | 3 | 4 | 5 | 6 | Comparative Example 1 | Control Serum |
|---|---|---|---|---|---|---|---|---|---|---|
| Composition | Hardly Water Soluble Polyoxyalkylene Derivative | wt % | 0.3 | 0.4 | 0.6 | 0.3 | 0.4 | 0.6 | 2.0 | — |
| | Polyvinylpyrrolidone | wt % | 1.0 | 1.0 | 1.0 | 1.0 | 1.0 | 1.0 | — | — |
| | Adsorptive Inorganic Substance | wt % | 2.0 | 2.0 | 2.0 | 2.0 | — | — | 2.0 | — |
| | Hydrolase | IU/mL | — | — | — | 1.0 | 10.0 | 45.0 | — | — |
| | Ion Exchange Water | wt % | 96.7 | 96.6 | 96.4 | 96.7 | 98.6 | 98.4 | 97.7 | — |
| Evaluation Result | Five Inversions | Blood Coagulation Time(min.) | 15 | 17 | 30 | 4 | 2 | 0.5 | 50 | — |
| | | Adhesion of Blood Clots on Inner Wall | No | No | No | No | No | No | No | — |
| | | Hemolysis | No | No | No | No | No | No | No | — |
| | One Inversion | Blood Coagulation Time(min.) | 16 | 18 | 32 | 5 | 3 | 1 | 63 | — |
| | | Adhesion of Blood Clots on Inner Wall | No | No | No | No | No | No | No | — |
| | | Hemolysis | No | No | No | No | No | No | No | — |
| | Ferritin Measurement (ng/mL) | ① | 56 | 55 | 55 | 56 | 56 | 56 | 56 | 56 |
| | | ② | 56 | 55 | 56 | 56 | 56 | 55 | 56 | 56 |

TABLE 2

| | | Unit | Example 7 | 8 | 9 | 10 | 11 | 12 | Comparative Example 2 | 3 | Control Serum |
|---|---|---|---|---|---|---|---|---|---|---|---|
| Composition | Hardly Water Soluble Polyoxyalkylene Derivative | wt % | 0.1 | 0.2 | 0.1 | 0.1 | 0.2 | 0.1 | 2.0 | — | — |
| | Partially Saponified Polyvinyl Alcohol | wt % | 0.1 | 0.1 | — | 0.1 | 0.1 | — | — | 1.0 | — |
| | Polyvinylpyrrolidone | wt % | 1.0 | 1.0 | 1.0 | 1.0 | 1.0 | 1.0 | 1.0 | 1.0 | — |
| | Adsorptive Inorganic Substance | wt % | 2.0 | 2.0 | 2.0 | 2.0 | — | — | 2.0 | 2.0 | — |
| | Hydrolase | IU/mL | — | — | — | 1.0 | 10.0 | 45.0 | — | — | — |
| | Ion Exchange Water | wt % | 96.8 | 96.7 | 96.9 | 96.8 | 98.7 | 98.9 | 95.0 | 96.0 | — |
| Evaluation Result | Five Inversions | Blood Coagulation Time(min.) | 15 | 17 | 15 | 4 | 2 | 0.5 | 31 | 31 | — |

TABLE 2-continued

|  |  | Unit | Example | | | | | | Comparative Example | | Control |
|---|---|---|---|---|---|---|---|---|---|---|---|
|  |  |  | 7 | 8 | 9 | 10 | 11 | 12 | 2 | 3 | Serum |
| One Inversion | Adhesion of Blood Clots on Inner Wall |  | No | No | No | No | No | No | No | Yes | — |
|  | Hemolysis |  | No | No | No | No | No | No | No | Yes | — |
|  | Blood Coagulation Time(min.) |  | 17 | 19 | 16 | 5 | 2 | 1 | 33 | 34 | — |
|  | Adhesion of Blood Clots on Inner Wall |  | No | No | No | No | No | No | No | Yes | — |
|  | Hemolysis |  | No | No | No | No | No | No | No | Yes | — |
| Ferritin Measurement (ng/mL) | ① |  | 56 | 55 | 55 | 56 | 56 | 55 | 36 | 55 | 56 |
|  | ② |  | 56 | 55 | 56 | 55 | 56 | 55 | 35 | 55 | 56 |

TABLE 3

|  |  | Unit | Example | | | | | | | | | | | | Control |
|---|---|---|---|---|---|---|---|---|---|---|---|---|---|---|---|
|  |  |  | 13 | 14 | 15 | 16 | 17 | 18 | 19 | 20 | 21 | 22 | 23 | 24 | Serum |
| Composition | Hardly Water Soluble Polyoxyalkylene Derivative | wt % | 0.1 | 0.3 | 0.2 | 0.2 | 0.2 | 0.2 | 0.1 | 0.3 | 0.2 | 0.1 | 0.2 | 0.2 | — |
|  | Water-soluble Silicone Oil | wt % | 0.05 | 0.05 | 0.01 | 0.05 | 0.05 | 0.05 | 0.05 | 0.05 | 0.01 | — | 0.2 | 0.001 | — |
|  | Partially Saponificated Polyvinyl Alcohol | wt % | 0.3 | 0.3 | 0.1 | 0.1 | 0.05 | 0.5 | 0.3 | 0.3 | 0.1 | 0.1 | 0.1 | 0.1 | — |
|  | Polyvinylpyrrolidone | wt % | 2.0 | 2.0 | 2.0 | 2.0 | 2.0 | 2.0 | 2.0 | 2.0 | 2.0 | 2.0 | 2.0 | 2.0 | — |
|  | Adsorptive Inorganic Substance | wt % | 2.5 | 2.5 | 2.5 | 2.5 | 2.5 | 2.5 | 2.5 | — | — | 2.5 | 2.5 | 2.5 | — |
|  | Hydrolase | IU/mL | — | — | — | — | — | — | 1.0 | 10.0 | 45.0 | — | — | — | — |
|  | Ion Exchange Water | wt % | 95.1 | 94.9 | 95.2 | 95.2 | 95.3 | 94.8 | 95.1 | 97.4 | 97.7 | 95.3 | 95.0 | 95.2 | — |
| Evaluation Result | Five Inversions | Blood Coagulation Time(min.) | 15 | 17 | 16 | 16 | 17 | 16 | 3 | 1 | 0.5 | 16 | 16 | 16 | — |
|  |  | Adhesion of Blood Clots on Inner Wall | No | No | No | No | No | No | No | No | No | No | No | No | — |
|  |  | Adhesion of Blood Clots on Rubber Plug | No | No | No | No | No | No | No | No | No | No | No | No | — |
|  |  | Hemolysis | No | No | No | No | No | No | No | No | No | No | No | No | — |
|  | One Inversion | Blood Coagulation Time(min.) | 16 | 19 | 17 | 18 | 20 | 19 | 4 | 1 | 0.5 | 18 | 19 | 19 | — |
|  |  | Adhesion of Blood Clots on Inner Wall | No | No | No | No | No | No | No | No | No | No | No | No | — |
|  |  | Adhesion of Blood Clots on Rubber Plug | No | No | No | No | No | No | No | No | No | Yes | No | Yes | — |
|  |  | Hemolysis | No | No | No | No | No | No | No | No | No | Yes | No | Yes | — |
| Ferritin Measurement (ng/mL) | ① |  | 55 | 55 | 56 | 56 | 56 | 54 | 55 | 55 | 55 | 56 | 51 | 55 | 56 |
|  | ② |  | 55 | 54 | 55 | 55 | 56 | 55 | 54 | 56 | 55 | 55 | 48 | 56 | 56 |

INDUSTRIAL APPLICABILITY

Since the blood coagulation promoter of the present invention includes at least one substance selected from the group consisting of (a) adsorptive inorganic substances and (b) hydrolases, and polyvinylpyrrolidone, it can exert excellent blood coagulation promoting ability and enable the blood to coagulate in short time.

In addition, since the blood coagulation promoter of the present invention includes a hardly water soluble polyoxyalkylene derivative and optionally a partially saponificated polyvinyl alcohol, it can exert excellent blood clot detaching ability, prevent coagulated blood from adhering to the inner wall of the blood collection tube in the form of blood clots, and detach the adhered blood clots.

Therefore, the blood coagulation promoter of the present invention exerts both excellent blood coagulation promoting ability and excellent blood clot detaching ability.

In the blood coagulation promoter of the present invention, when it further includes $3 \times 10^{-3}$ to 7 parts by weight of water-soluble silicone oil, relative to 100 parts by weight of the sum of hardly water soluble polyoxyalkylene derivative; partially saponificated polyvinyl alcohol added as necessary; at least one substance selected from the group consisting of (a) adsorptive inorganic substances and (b) hydrolases capable of hydrolyzing a bond between Arg and an arbitrary amino acid reside and/or a bond between Lys and an arbitrary amino acid residue in a peptide chain; and the polyvinylpyrrolidone, the blood clot detaching ability against the inner wall of the tube is further improved. In addition, excellent blood clot detaching ability is exerted against the plug member of the blood collection tube. In addition, since the water-soluble silicone oil is not included as high concentration as the conventional case, hemolysis hardly occurs. Therefore, test values will not be adversely affected.

Furthermore, since the blood collection tube of the present invention accommodates the blood coagulation promoter of the present invention, it is possible to provide a blood collection tube having improved blood coagulation promoting ability and improved blood clot detaching ability.

The invention claimed is:

1. A blood coagulation promoter comprising:
(A) a glycerin derivative of polyoxyalkylene;
(B) at least one substance selected from the group consisting of (i) an adsorptive inorganic substance and (ii) a hydrolase capable of hydrolyzing a bond between Arg and an arbitrary amino acid residue and/or a bond between Lys and an arbitrary amino acid residue in a peptide chain; and
(C) polyvinylpyrrolidone,
wherein the adsorptive inorganic substance is selected from the group consisting of silica, glass, kaolin, celite, and bentonite.

2. The blood coagulation promoter according to claim 1, further comprising $3 \times 10^{-3}$ to 7 parts by weight of water-soluble silicone oil, relative to 100 parts by weight of the sum of:
(A) the glycerin derivative of polyoxyalkylene;
(B) the at least one substance selected from the group consisting of (i) an adsorptive inorganic substance and (ii) a hydrolase capable of hydrolyzing a bond between Arg and an arbitrary amino acid residue and/or a bond between Lys and an arbitrary amino acid residue in a peptide chain; and
(C) the polyvinylpyrrolidone.

3. The blood coagulation promoter according to claim 1, further comprising a polyvinyl alcohol obtained by partial saponification.

4. The blood coagulation promoter according to claim 3, further comprising $3 \times 10^{-3}$ to 7 parts by weight of water-soluble silicone oil, relative to 100 parts by weight of the sum of:
(A) the glycerin derivative of polyoxyalkylene;
(B) the polyvinyl alcohol obtained by partial saponification;
(C) the at least one substance selected from the group consisting of (i) an adsorptive inorganic substance and (ii) a hydrolase capable of hydrolyzing a bond between Arg and an arbitrary amino acid residue and/or a bond between Lys and an arbitrary amino acid residue in a peptide chain; and
(D) the polyvinylpyrrolidone.

5. A blood collection tube formed of a tubular vessel having a bottom accommodating the blood coagulation promoter of any one of claims 1 to 4.

6. The blood coagulation promoter of any one of claims 1 to 4, wherein the glycerin derivative of polyoxyalkylene is a glycerin derivative of polypropylene glycol.

7. The blood coagulation promoter according to claim 3, wherein the polyvinyl alcohol obtained by partial saponification has a saponification degree of 75 to 98% by mole.

8. The blood coagulation promoter according to claim 3, wherein the polyvinyl alcohol obtained by partial saponification has a degree of polymerization of 300 to 3,500.

9. The blood coagulation promoter of any one of claims 1 to 4, wherein the adsorptive inorganic substance (a) is in powder form, (b) has a specific surface area of 10 to 1000 $m^2/g$, and (c) has an average particle size of less than or equal to 50 μm.

10. The blood coagulation promoter according to claim 2, wherein the water-soluble silicone oil is at least one selected from the group consisting of aliphatic silicone oils and aromatic silicone oils.

11. The blood coagulation promoter according to claim 1, further comprising an antifibrirolytic agent and/or antiplasmin agent.

* * * * *